US006313913B1

(12) United States Patent
Nakagawa et al.

(10) Patent No.: US 6,313,913 B1
(45) Date of Patent: *Nov. 6, 2001

(54) SURFACE INSPECTION APPARATUS AND METHOD

(75) Inventors: Yumi Nakagawa, Kowasaki; Koichiro Komatsu, Setagaya-ku, both of (JP)

(73) Assignee: Nikon Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/447,691

(22) Filed: Nov. 23, 1999

(30) Foreign Application Priority Data

Nov. 26, 1998 (JP) .................................................. 10-335855

(51) Int. Cl.⁷ .................................................... G01N 21/00
(52) U.S. Cl. .................................. 356/237.2; 356/237.6; 356/394; 250/225
(58) Field of Search .............................. 356/237.1, 237.2, 356/237.3, 237.5, 237.4, 237.6, 394, 239.7, 239.8; 250/225, 560, 561

(56) References Cited

U.S. PATENT DOCUMENTS

| 4,468,120 | * | 8/1984 | Tanimoto et al. | ................. | 356/237.1 |
| 5,473,426 |   | 12/1995 | Hayano et al. | ................. | 356/237 |
| 5,856,868 |   | 1/1999 | Kato et al. | ................. | 356/237 |
| 5,907,396 | * | 5/1999 | Komatsu et al. | ................. | 356/237.1 |

FOREIGN PATENT DOCUMENTS

| 36-0011844-A | * | 1/1985 | (JP) . |
| 40-6229935-A | * | 8/1994 | (JP) . |

* cited by examiner

*Primary Examiner*—Frank G. Font
*Assistant Examiner*—Sang H. Nguyen
(74) *Attorney, Agent, or Firm*—Oliff & Berrige, PLC

(57) ABSTRACT

A surface inspection apparatus is provided which uses at least two sets of surface inspection systems each comprising with a paired surface illumination device (A1, B1) and detection device (A2, B2), with each set of illumination devices and detection devices creating their own irradiation regions (51A, 51B) and detection regions (23A,23B), in which the irradiation and detection regions of one pair of illumination and detection devices does not over lap the illumination and detection regions of the adjacent pair of illumination and detection devices. The surface illumination devices preferably project light at an angle of 80° or more with respect to a normal to the surface being inspected (21). The detection devices detect light scattered by dust or defects on the surface to be inspected. The surface to be inspected can be moved in a direction perpendicular to the direction of the illumination and detection regions on the surface being inspected. Thus, the entire surface can be inspected. The inspection device and method can also be adapted for use in a liquid crystal display manufacturing operation.

11 Claims, 8 Drawing Sheets

SURFACE INSPECTION APPARATUS AND METHOD

FIELD OF THE INVENTION

The present invention relates to a method and apparatus to inspect a surface for defects, flaws and foreign matter and a method and apparatus which can also automatically detect flaws and foreign matter, such as fine particulate matter, on the surface being inspected. The present invention also relates to a method for manufacturing liquid crystal displays.

BACKGROUND OF THE INVENTION

In photolithography, a circuit pattern is formed by a reticle or photomask (hereinafter referred to simply as a "mask") on a substrate or wafer. The mask is typically a sheet of glass or similar material on which are formed patterns made from chromium or chrom-oxide. Stretched across the top of the mask is a pellicle which protects the mask from foreign matter such as dust and the like. The pattern of the mask is transferred onto the substrate during the photolithography process. However, if foreign matter such as large particles adhere to the pellicle, the image of the foreign matter will affect the pattern formed on the semiconductor wafer, resulting in a defective circuit pattern. Any defects in the circuit patterns in turn results in a reduction in manufacturing yield. Consequently, to assure defect free transfer of the pattern to the wafer prior to exposure of the pattern on the mask onto the wafer surface, the pellicle must be inspected to verify that foreign matter is not present.

FIG. 7 is a schematic perspective view from an oblique angle of the structure of a conventional foreign matter inspection apparatus as disclosed in U.S. Pat. No. 5,473,426. The apparatus shown in FIG. 7 emits from semiconductor laser 11 a radial beam of laser light of approximately 780 nm wavelength. The beam of laser light is transformed into a parallel beam by collimator lens 12. The beam is then expanded in the X direction in FIG. 7 by anamorphic prism 13 to produce a laser light beam with an elliptical cross section perpendicular to the X direction. Stop 14, which has a parallelogram-shaped aperture, then partially blocks the beam in the longitudinal or X direction. Mirror 15 then reflects the beam onto the surface to be inspected, pellicle 21, at an angle of incidence θ close to 90° as measured with respect to the surface normal of pellicle 21.

The beam of light reflected onto pellicle 21 by mirror 15 forms a band-shaped illumination region 30 extending in the X direction across the pellicle 21. Band-shaped irradiation region 30 constitutes the region on pellicle 21 to be inspected. Foreign matter present in this band-shaped illumination region 30 scatters the light incident the region. The scattered light from the foreign matter passes through light receiving lens 31, and forms an image on linear image sensor 20. The intensity of the scattered light detected by linear image sensor 20 helps determine the size of the foreign matter. The system inspects the entire surface of the pellicle 21 spread across mask 22 for foreign matter by moving the mask 22 and pellicle 21 in a direction perpendicular to the direction of the band-shaped illumination region 30, the Y direction in FIG. 7, so that the band-shaped illumination region 30 moves across the entire surface of pellicle 21. Thus, the conventional inspection system depicted in FIG. 7 has one optical system which combines an incident light system with a receiving light system.

The trend in the semiconductor industry has been to use larger masks with much finer circuit detail. As a consequence, the reduction ratio of the projection lens in photolithography equipment is often increased from 4× to 8×. Thus, larger masks are needed to exposure the same area. This has increased the size of the area to be inspected while at the same time requiring inspection systems which are more sensitive. In the liquid crystal display industry, larger and preciser displays are required. To meet these needs conventional inspection systems, which must view a larger inspection region with the same or larger numerical aperture, have had to have the diameter of the light receiving lens and the size of other parts of the inspection system increased. The larger inspection systems (in particular the light receiving portion of the systems) also require a larger amount of space. The use of larger parts has increased the costs of these systems and has resulted in lower yields. The size of the incident light systems have also increased attendant with the increase in the size of the inspection region.

Additionally, use of one light receiving system in conventional inspection apparatus of increasingly larger size has also resulted in a significant difference in the sensitivity of detecting foreign matter between the center and the edges of the larger inspection regions. Thus, the system becomes much less sensitive to foreign matter towards the periphery of the inspection region viewed. This is in part due to the fact that the angle of the optical axis of the light receiving system with the region to be inspected varies greatly between the center and edges of the region being inspected.

SUMMARY OF THE INVENTION

The present invention addresses the problems in the prior art with the purpose of reducing the space required by the entire apparatus, i.e., making it compact, and providing a surface inspection method and apparatus with superior accuracy. The present invention also has the purpose of providing an accurate and effective method of manufacturing a liquid crystal display using the surface inspection method and apparatus.

A first aspect of the invention is a surface inspection system comprising a first light irradiation system that irradiates a surface to be inspected with a first beam of electromagnetic radiation (hereinafter, "light") beam which forms a first band-shaped irradiation region along a predetermined first direction (X axis direction) on the surface to be inspected; a first light receiving system that receives scattered light from first band-shaped irradiation region; a second light irradiation system that irradiates the surface to be inspected with a second light beam which forms second band-shaped irradiation region along the first direction (X axis direction) on the surface to be inspected; a second light receiving system that receives scattered light from second band-shaped irradiation region; and a scanning mechanism that moves the first and second light irradiation systems and surface to be inspected with relative motion along a second direction (Y axis direction) substantially orthogonal to the first direction (X axis direction), in which the first band-shaped irradiation region and second band-shaped irradiation region are configured so that they are formed on surface to be inspected separated by just predetermined distance d along the second direction (Y axis direction). This assures the entire surface to be inspected is scanned during the inspection process.

In a second aspect of the present invention the first band-shaped irradiation region and the second band-shaped irradiation region are formed on the surface to be inspected separated from each other by a predetermined distance along the second direction (Y axis direction) to assure the irradiation regions do not overlap and create interference between the sets of inspection apparatuses.

A third aspect of the invention is a method for inspecting a surface which includes the steps of: forming a first illumination region on a surface to be inspected; detecting light scattered from said first illumination region; forming a second illumination region on a surface to be inspected; detecting light scattered from said second illumination region; and moving the surface to be inspected in a direction which allows said first and second illumination regions to move across an entire portion of the surface to be inspected.

A fourth aspect of the present invention is a liquid crystal display manufacturing method, including: inspecting a reticle for defects and foreign matter adhering to said reticle; forming with the reticle, after the inspecting step determines the reticle is free of defects and foreign matter, a pattern on the reticle onto a photosensitive substrate. The step of inspecting said reticle comprises forming a first irradiation region by irradiating said reticle with a first beam of electromagnetic radiation, then detecting scattered electromagnetic radiation from said first irradiation region, then forming a second irradiation region having a predetermined relationship with said first irradiation region by irradiating said reticle with a second beam of electromagnetic radiation, and then detecting scattered electromagnetic radiation from said second irradiation region.

A fifth aspect of the present invention is a reticle inspection method which includes the steps of: forming a first irradiation region on the reticle by irradiating the reticle with a first beam of electromagnetic radiation; detecting scattered electromagnetic radiation from said first irradiation region; forming a second irradiation region having a predetermined relationship with said first irradiation region by irradiating said reticle with a second beam of electromagnetic radiation from a predetermined position; detecting scattered electromagnetic radiation from said second irradiation region; and wherein the system is able to detect from the scattered electromagnetic radiation whether or not the reticle has any defects any foreign matter adhering to its surface or to the surface of a pellicle arranged adjacent thereto.

BRIEF DESCRIPTION OF THE DRAWINGS

FIG. 8 (B) is a schematic plan view of a second embodiment of the present invention which uses three sets of detection optical systems each of which is arranged so that light receiving take-in regions do not overlap adjacent irradiation regions on the surface to be inspected.

DETAILED DESCRIPTION OF THE INVENTION

The following detailed description, with the aid of the drawings, describes several embodiments of the present invention and methods for practicing the present invention. Items that are identical or equivalent in each drawing are assigned the identical or similar symbols. Redundant explanations are omitted.

Figure 1:
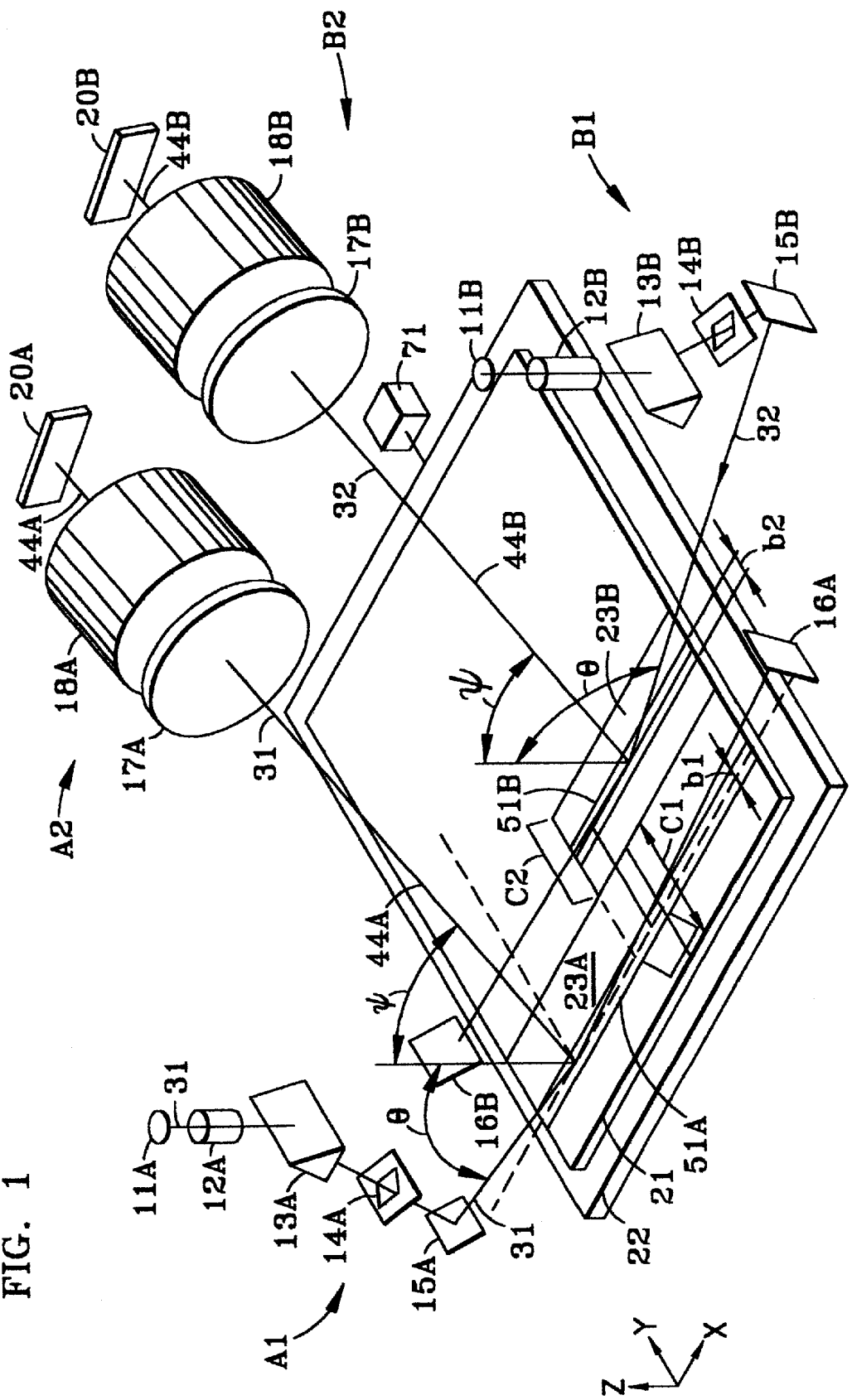
FIG. 1 is a schematic perspective diagram of the surface inspection apparatus of a first embodiment for carrying out the present invention.

FIG. 1 is a schematic perspective diagram from an oblique angle of a first embodiment of the surface inspection system of the present invention used in the practice of the method of the present invention.

For reference purposes, an XYZ Cartesian coordinate system is defined in FIG. 1, with the X direction being the direction in which the longitudinal band-shaped irradiation regions 51A and 51B are projected onto pellicle 21, the surface to be inspected. The Y direction, perpendicular to the X direction, is the direction in which the surface to be inspected is scanned during the inspection process. Pellicle 21 and mask 22 thus move in the Y direction during the scanning process. The Z direction is perpendicular to the plane formed by the X and Y axis, with the surface to be inspected, pellicle 21, positioned in the X and Y plane.

In FIG. 1, a first irradiation system A1 projects light at an oblique angle to form a first band-shaped irradiation region 51A on the surface to be inspected 21. The first irradiation system A1 does so by first emitting laser light 31 (lines designated light beams are only meant to indicate the path the light travels and do not represent the actual structure of the beam) from semiconductor laser 11A. Light 31 is then formed into a parallel beam via collimator lens 12A. The parallel beam of laser light then enters anamorphic prism 13A, which expands laser light 31 in the X direction. Laser light 31 thus takes on an elliptically shaped cross-section perpendicular to the X direction. Laser light 31 is then partially blocked in the longitudinal direction, the X direction, by an aperture stop 14A having a parallelogram-shaped aperture. Laser light 31 is then reflected by a mirror 15A onto surface to be inspected 21, at an incident angle θ, close to 90°. Here, incident angle θ is measured from the normal to the X-Y plane, the Z axis, towards the X axis. Incident angle θ should be at least 80° or greater, and is preferably 85° or greater, and even more preferably 89° or greater. Pellicle 21 is affixed to mask 22 via a frame and is spread out substantially parallel to the XY plane. A drive/scanning mechanism 71 is configured to move mask 22 and consequently pellicle 21 in the Y direction. This enables scanning of first band-shaped irradiation region 51A across the surface of pellicle 21. Drive/scanning mechanism 71 and the way it functions is well known in the art and accordingly is not described in detail herein.

Light beam 31 which impinges substantially parallel to the surface of pellicle 21 (i.e., at an angle of incidence θ greater than 80°) forms first band-shaped irradiation region 51A along the X direction of the surface of pellicle 21. A direct light absorbing body 16A absorbs the specularly reflected light from pellicle 21. However, scattered light from any foreign matter (not shown) on pellicle 21 is received by first light receiving system A2, positioned along the Y direction, at light receiving angle ψ close to 90°. In a preferred embodiment, light receiving angle ψ is set at 80° or greater. The scattered light from the foreign object enters first light receiving system A2 via a sharp cut filter 17A and a light receiving lens 18A which passes it onto an image sensor 20A. Sharp cut filter 17A blocks disturbance light having a wavelength below the visible light range, i.e., about 600 nm. This disturbance light forms noise on the so-called scattered signal depending on the light intensity of the scattered light. Image sensor 20A can be a standard detection device or photoelectric detector such as a one-dimensional CCD.

A second irradiation system B1 is provided at a position opposite first irradiation system A1 with pellicle 21 positioned between them. Second irradiation system B1 projects a second beam of laser light 32 at an oblique incident angle θ, one greater than 80° from the Z axis, onto to pellicle 21 which forms the second band-shaped irradiation region 51B at a position offset in the Y direction with respect to first band-shaped irradiation region 51A on pellicle 21 by distance d as depicted in FIG. 1, FIG. 2 and FIG. 5A. Second irradiation system B1 has the identical configuration as first irradiation system A1 and, as shown in FIG. 1. Second irradiation system B1 thus has all of the same components: a semiconductor laser 11B for producing a beam of laser light, collimator lens 12B which forms it into a parallel beam, anamorphic prism 13B which extends the beam in the direction of the X axis, stop 14B which partially blocks the beam and mirror 15B which reflects it towards the surface of pellicle 21. Also, in a preferred embodiment, angle θ is 85° or greater, and is more preferably 89° or greater.

An absorbing body 16B (shielding body) is positioned opposite second irradiation system B1 with pellicle 21 positioned in between. Absorbing body 16B eliminates specularly reflected light created by second irradiation system B1 by absorbing light reflected off pellicle 21.

Figure 2A:
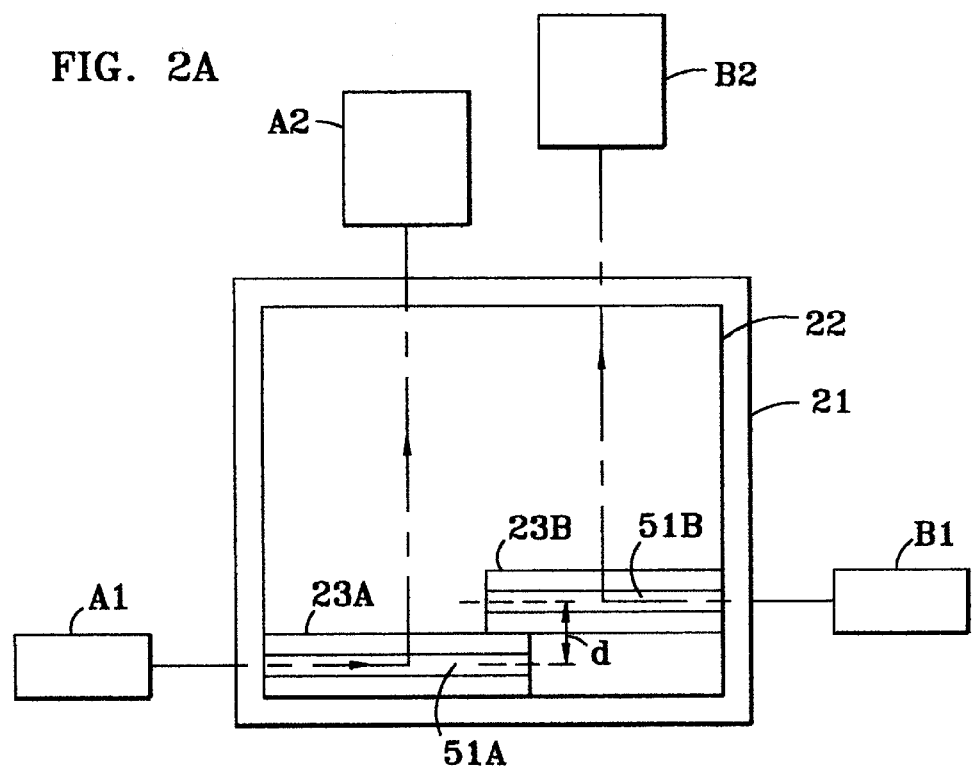
FIG. 2A is a plan view that depicts the surface inspection apparatus and the illumination and detection regions, according to the first embodiment of the present invention of FIG. 1.

If foreign matter, such as dust, is present in second band-shaped irradiation region 51B when formed on pellicle 21 by second irradiation system B1, the foreign matter generates scattered light. The scattered light created by dust or other foreign matter in the second band-shaped irradiation region 51B is detected by second light receiving system B2. Second light receiving system B2 is positioned with respect to first light receiving system A2 a preset distance along the Y axis. This preset distance corresponds to d, the distance between the center lines of first band-shaped irradiation region 51A and second band-shaped irradiation region 51B, as depicted in FIG. 2A. Second light receiving system B2 functions in the same manner as first light receiving system A2. Second light receiving system B2 has the identical configuration as first light receiving system A2 and thus has the same components, which includes among other things, a sharp cut filter 17B, a light receiving lens 18B and an image sensor 20B.

Figure 2B:
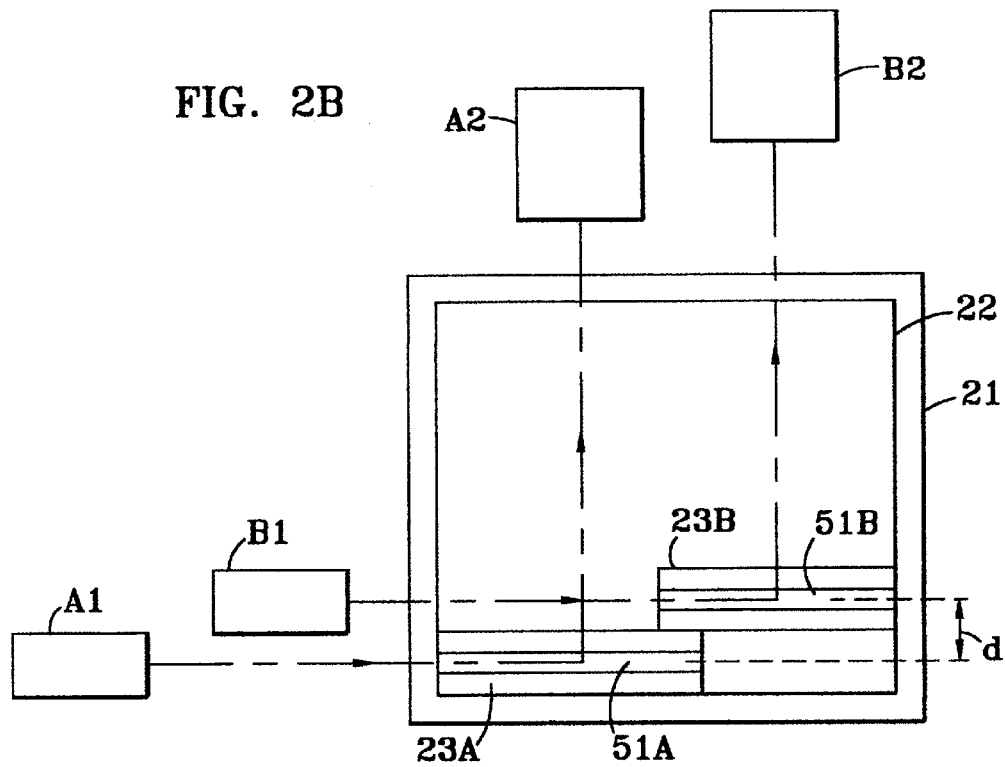
FIG. 2B is a plan view that depicts an alternative configuration of the surface inspection apparatus, according to the first embodiment of the present invention of FIG. 1.

FIG. 2A is a schematic plan view of the configuration of the essential elements for practicing the present invention shown in FIG. 1. FIG. 2B shows an alternative arrangement for practicing the present invention in which the second irradiation system B1 and the first irradiation system A1 are on the same side of the surface to be inspected, pellicle 21. As depicted in FIG. 2B, the second band-shaped irradiation region 51B is separated from the first band-shaped irradiation region 51A by predetermined distance d in the Y direction.

In the first embodiment of the present invention shown in FIG. 1, predetermined distance d is set so that light receiving take-in region 23A and light receiving take-in region 23B do not overlap.

Light receiving take-in region 23A corresponds to the light receiving surface (photoelectric detection surface) of first light receiving member 20A of first light receiving system A2. Light receiving take-in region 23B corresponds to the light receiving surface (photoelectric detection surface) of second light receiving member 20B of the second light receiving system B2. Accordingly, first band-shaped light receiving take-in region 23A is the optical conjugate of the light receiving surface (photoelectric detection surface) of light receiving member 20A of first light receiving system A2. The second band-shaped light receiving take-in region 23B is the optical conjugate of the light receiving surface (photoelectric detection surface) of light receiving member 20B of second light receiving system B2. Thus, the detection surfaces of light receiving members 20A and 20B define the size of their corresponding light receiving take-in regions 23A and 23B located on the surface to be inspected.

Predetermined distance d of the present invention will now be explained in more detail with the aid of FIGS. 5A, 5B and 5C.

FIG. 5A is a schematic plan view depicting the positions of band-shaped irradiation regions 51A and 51B and band-shaped light receiving take-in regions 23A and 23B in the first embodiment of the present invention of FIG. 1. In FIG. 5A, the width at the surface to be inspected 21 of band-shaped irradiation region 51A of first irradiation system A1 is b1, and the width at the surface to be inspected 21 of band-shaped light receiving take-in region 23A of first light receiving system A2 is c1. In this embodiment for carrying out the present invention, the following relationship applies: b1<c1. As shown in FIG. 5A, the centerline in the longitudinal direction of first band-shaped irradiation region 51A formed on the surface to be inspected, pellicle 21, by first irradiation system A1 coincides with the centerline in the longitudinal direction of first band-shaped light receiving take-in region 23A of first light receiving system A2 on the surface to be inspected 21. In other words, band-shaped irradiation region 51A overlaps with lateral symmetry in substantially the center of the band of band-shaped light receiving take-in region 23A. The width at the surface to be inspected 21 of band-shaped irradiation region 51B of second irradiation system B1 is b2, and the width at the surface to be inspected 21 of band-shaped light receiving take-in region 23B of second light receiving system B2 is c2. In this embodiment for carrying out the present invention the following relationship applies: b2<c2. Also, as depicted in FIG. 5A, the centerline in the longitudinal direction of second band-shaped irradiation region 51B formed on the surface to be inspected (pellicle 21) by second irradiation system B1 coincides with the centerline in the longitudinal direction of second band-shaped light receiving take-in region 23B of second light receiving system B2 on the surface to be inspected, pellicle 21. In addition, in the example shown in FIG. 5A, the following relationship applies: $b1+c2<b2+c1$. The distance d between these band-shaped regions refers to the distance between the center lines in the lateral direction.

As depicted in FIG. 5A, first band-shaped irradiation region 51A and first band-shaped light receiving take-in region 23A coincides by distance a with second band-shaped irradiation region 51B and second band-shaped light receiving take-in region 23B in the longitudinal direction. This overlap by of longitudinal distance a covered by both sets of bands 51A and 23A of 51B and 23B assures the entire surface to be inspected will be covered with no inadvertently omitted inspection areas on the surface to be inspected.

In the case of FIG. 5A, the first and second light irradiation systems and the first and second light receiving systems are arranged so that band-shaped light receiving take-in regions 23A and 23B of the first and second light receiving systems do not mutually overlap the same area at the same time on the surface to be inspected. Namely, the two light irradiation systems are arranged so that distance d between the longitudinal centerline of each band-shaped light receiving take-in regions 23A and 23B of the first and second light receiving systems is greater than or equal to $(c1+c2)/2$. Since the light receiving take-in regions 23A and 23B do not mutually overlap, the irradiation regions 51A and 51B also do not mutually overlap, given the fact the irradiation regions of each are narrower in the direction of the Y axis than the light receiving regions as indicated by the relationships $b1<c1$ and $b2<c2$. Thus, by assuring the relationships $(c1+c2)/2$ and $b1<c1$ and $b2<c2$ exist between inspection systems A1 and A2 and inspection systems B1 and B2, it can be assured light from one does not interfere with the functioning of the other.

Figure 5C:
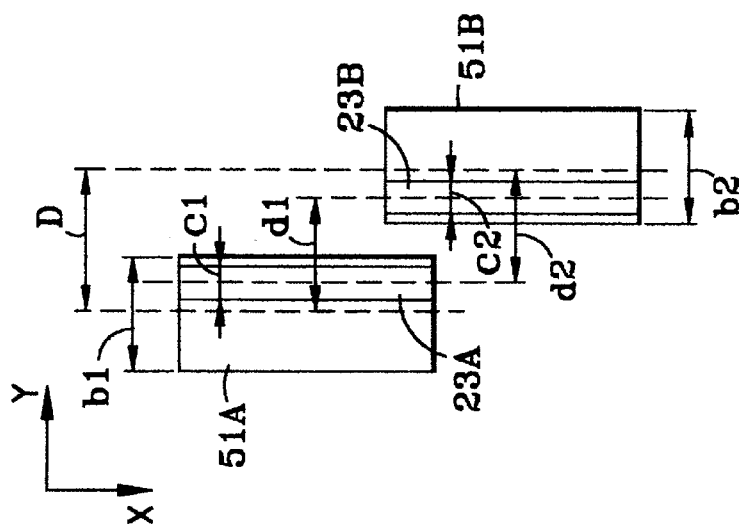
FIG. 5C is a schematic plan view which depicts the relationship between the first and second band-shaped irradiation regions and the first and second band-shaped light receiving take-in regions of a second alternative embodiment.
Figure 5B:
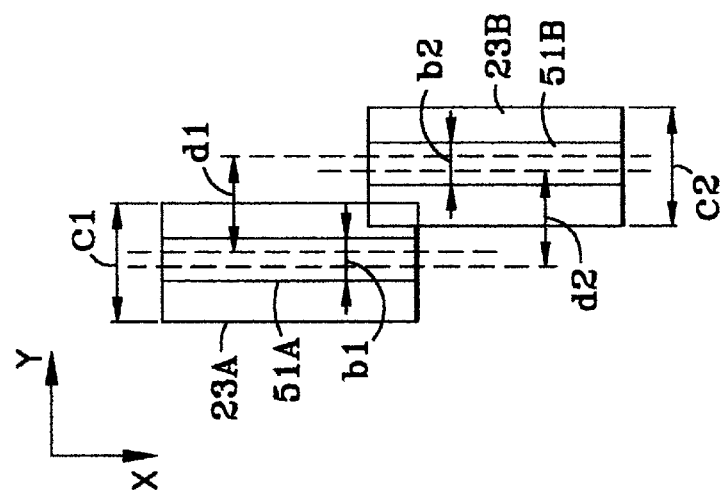
FIG. 5B is a schematic plan view which depicts the relationship between the first and second band-shaped irradiation regions and the first and second band-shaped light receiving take-in regions of a first alternative embodiment.
Figure 5A:
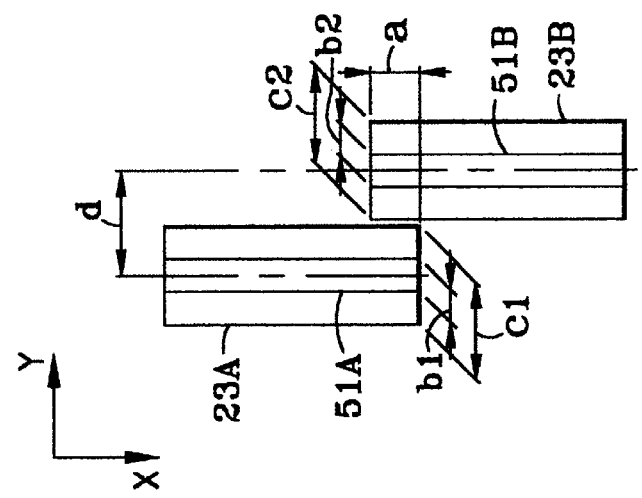
FIG. 5A is a schematic plan view which depicts the relationship between the first and second band-shaped irradiation regions and the first and second band-shaped light receiving take-in regions of the first embodiment of the present invention.

FIG. 5B and FIG. 5C provide alternative examples of systems in which the center lines of irradiation region 51A and light receiving take-in region 23A do not coincide, and the center lines of irradiation region 51B and light receiving take-in region 23B do not coincide.

In the case of FIG. 5B, first and second light irradiation systems A1 and B1 and first and second light receiving systems A2 and B2 are set so that distance d1 between the longitudinal centerline of band-shaped irradiation region 51A of first irradiation system A1 and the longitudinal centerline of band-shaped light receiving take-in region 23B of second light receiving system B2 is larger than $(b1+c2)/2$. In addition, distance d2 between the longitudinal centerline of band-shaped irradiation region 51B of second light receiving system B2 and the longitudinal centerline of band-shaped light receiving take-in region 23A of first light receiving system A2 is larger than $(b2+c1)/2$. If so arranged, part of light receiving take-in regions 23A and 23B of the two light receiving systems A2 and B2 overlap. However, the light receiving take-in region on one side does not overlap the irradiation region on the other side. Accordingly, the light from the irradiation receiving system A1 and A2 does not interfere with irradiation receiving system B1 and B2. Likewise, light from irradiation receiving system B1 and B2 does not interfere with irradiation receiving system A1 and A2.

As described above and depicted in FIG. 5B, the system can still function properly when the light receiving regions 23A and 23B of system A2 and B2 respectively overlap, so long as light irradiation regions 51A and 51B do not overlap. However, a preferred embodiment of the system is as depicted in FIG. 5A, where light irradiation region 51A and light receiving region 23A do not overlap light irradiation region 51B and light receiving region 23B.

FIG. 5A and FIG. 5B depict cases in which c1 and c2 of the band-shaped light receiving take-in regions are larger than widths b1 and b2 of the band-shaped irradiation regions, respectively. FIG. 5C, on the other hand, depicts the situation in which widths b1 and b2 of the band-shaped irradiation regions are larger than widths c1 and c2 of the band-shaped light receiving take-in regions. In the example shown in FIG. 5C, d1 is the distance between the centerline along the longitudinal direction of band-shaped irradiation region 51A of first irradiation system A1 and the centerline along the longitudinal direction of second band-shaped light receiving take-in region 23B of second light receiving system B2, d2 is the distance between the centerline along the longitudinal direction of band-shaped light receiving take-in region 23A of first light receiving system A2 and the centerline along the longitudinal direction of second band-shaped irradiation region 51B of second irradiation system B1. Further, D is the distance between the centerline along the longitudinal direction of band-shaped irradiation region 51A of first irradiation system A1 and the centerline along the longitudinal direction of second band-shaped irradiation region 51B of second irradiation system B1.

If the example shown in FIG. 5C is arranged so that centerline spacing D between band-shaped irradiation regions 51A, 51B satisfies $D>(b1+b2)/2$, the irradiation regions do not mutually overlap, and the effects of stray light due to strong irradiation can be avoided. Moreover, if arranged so that $d1>(b1+c2)/2$ and $d2>(b2+c1)/2$ are satisfied as shown in at least FIG. 5B, then even if part of the light take-in regions mutually overlap, the light from the overlapping part is not taken into the other's band-shaped light receiving take-in region.

Figure 3:
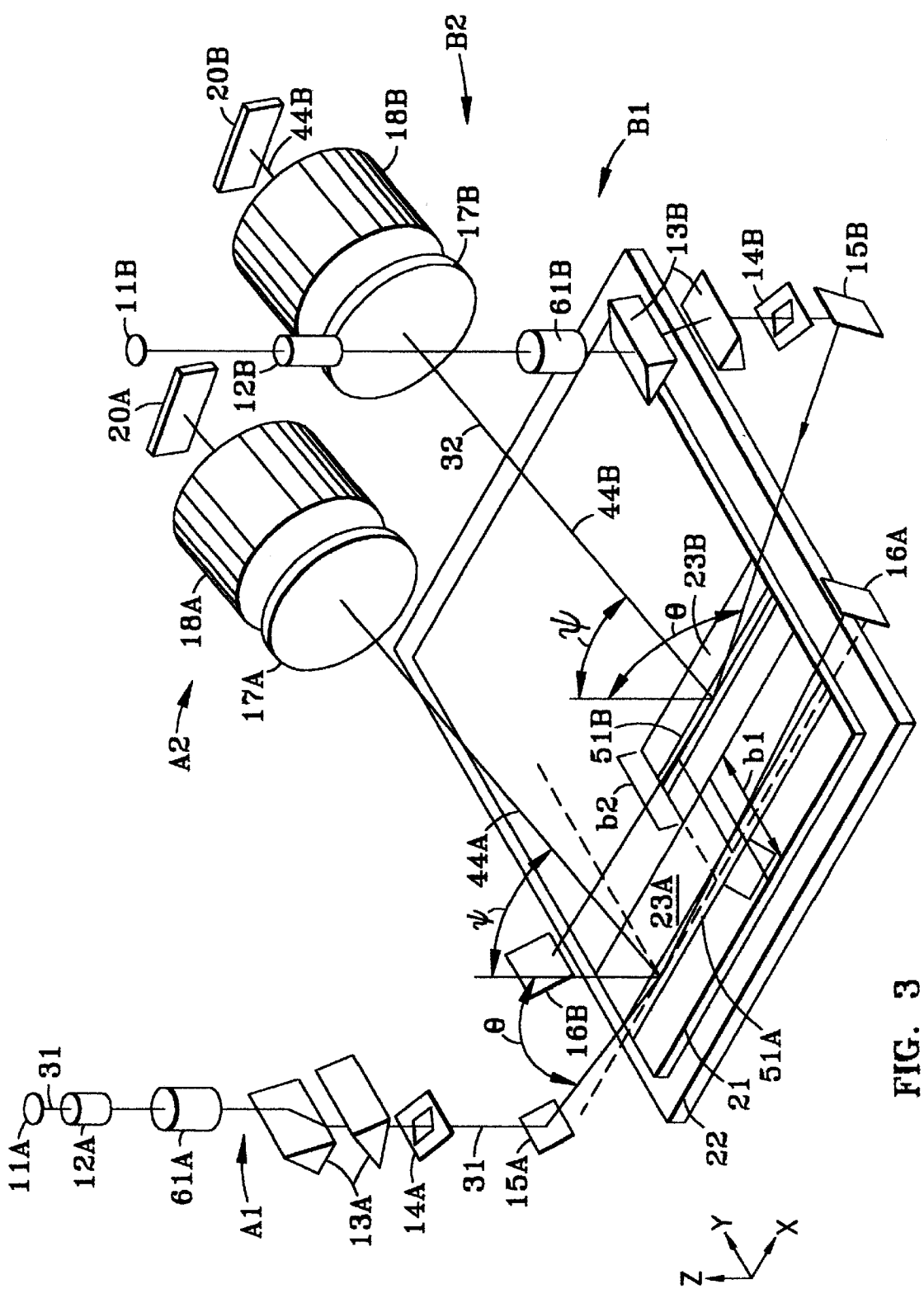
FIG. 3 is a schematic perspective view of the surface inspection apparatus of a second embodiment of the present invention.

FIG. 3 provides a schematic perspective view of a second embodiment of the surface inspection apparatus and method of the present invention. The XYZ Cartesian coordinate system is the same as that in FIG. 1. The apparatus of the second embodiment of the present invention depicted in FIG. 3 has the same configuration as the apparatus of the first embodiment of the present invention depicted in FIG. 1 and differs only in that the incident light systems A1 and B1 (irradiation systems) respectively include beam expanders 61A and 61B and also two anamorphic prisms 13A and 13B to accommodate an increased size of the surface to be inspected. The following description explains the configuration depicted in FIG. 3, with attention being given to the aspects in which it differs from the apparatus shown in FIG. 1.

In FIG. 3, the laser light 31 emitted by semiconductor laser 11A forms a parallel light beam via collimator lens 12A, which then enters beam expander 61A. The diameter of the beam of laser light 31 that enters beam expander 61A is expanded in the X and Y directions and then enters anamorphic prisms 13A. Anamorphic prisms 13A then expands laser light 31 in the X direction such that its cross section is elliptical. Laser light 31 then enters stop 14A, which has a parallelogram-shaped aperture, the sides of which are projected parallel to the X-direction, and then is reflected by a mirror 15A onto surface to be inspected 21. Incident angle θ, which is the angle laser light 31 makes with the Z axis, is close to 90°. The arrangement of first light receiving system A2 and the light receiving method of the second embodiment are the same as that of the first embodiment shown in FIG. 1. Accordingly, an explanation of this system in the present embodiment omitted.

Irradiation system B1 and light receiving system B2 of the second embodiment of the present invention as depicted in FIG. 3 are symmetric in the direction of the Y axis with irradiation system A1 and light receiving system A2 of the second embodiment. Additionally, aside from the addition of a beam expander 61B and two anamorphic prisms 13B, the system depicted in FIG. 3 functions the same as that depicted in FIG. 1. Direct light absorbing body 16B that absorbs the specularly reflected light from pellicle 21 is also the same as previously described.

Additionally, irradiation systems A1 and B1 in the embodiment depicted in FIG. 3 are positioned so that light receiving take-in region 23A of first light receiving system A2 and light receiving take-in region 23B of second light receiving system B2 are separated by distance d and do not overlap.

As noted above in the second embodiment for carrying out the present invention, beam expanders 61A and 61B are added, and two anamorphic prisms 13A and 13B are employed in both A1 and B1. Consequently, the irradiation region can be enlarged, and the invention can be applied to the inspection of a surface to be inspected larger than that of the apparatus in the first embodiment in FIG. 1 for carrying out the present invention.

The first and second embodiments of the present invention depicted in FIGS. 1 and 3 show two different inspection optical systems which use two sets of optical systems, the first system being A1 and A2 and the second system being B1 and B2. However, the system of the present invention can be practiced with three or more paired irradiation and light receiving systems to cover a larger surface to be inspected, mentioned later.

Figure 4:
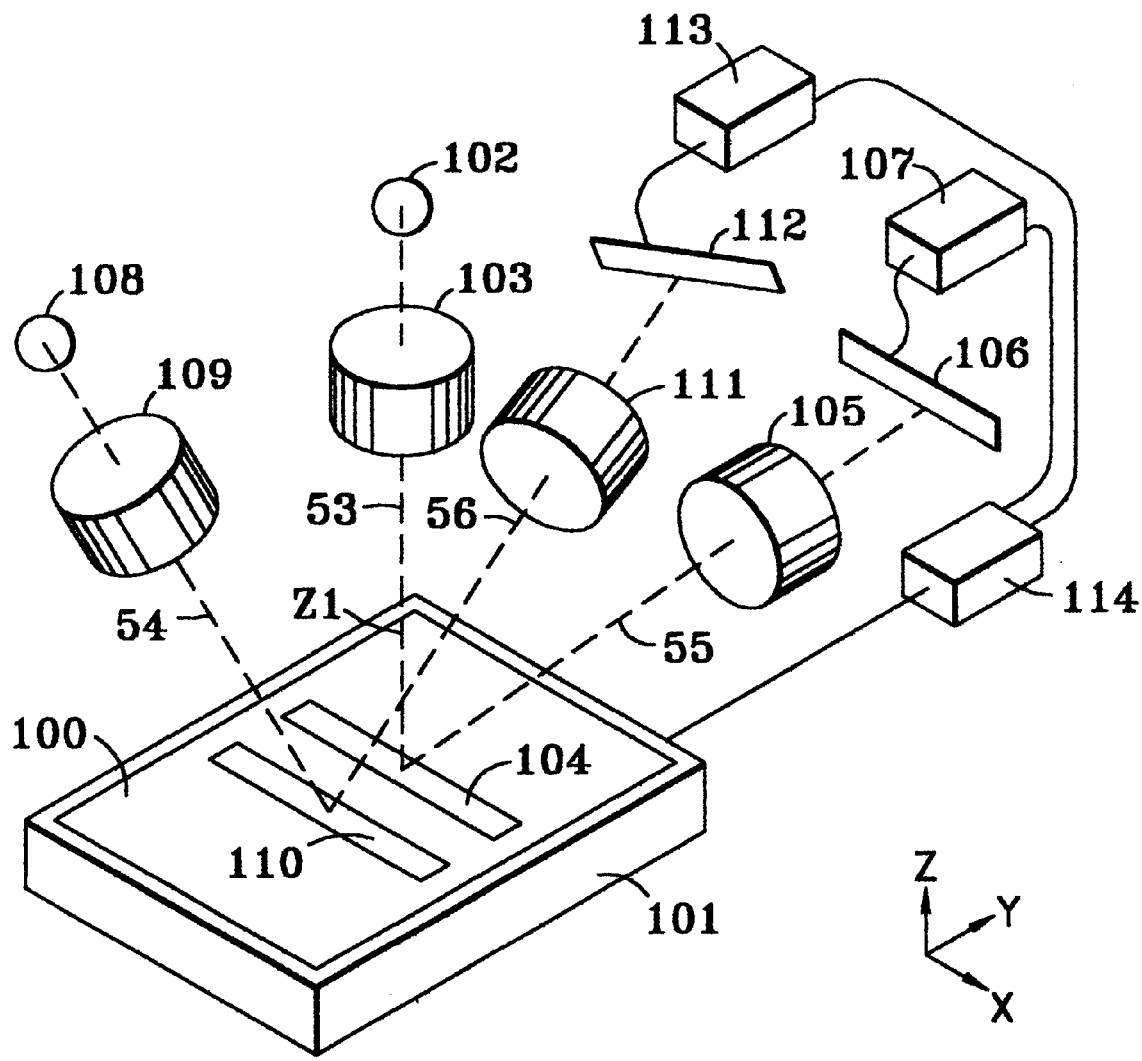
FIG. 4 is a schematic perspective view of a third embodiment of the surface inspection apparatus of the present invention.

The following describes a third embodiment depicted in FIG. 4 of the present invention configured as a liquid crystal substrate surface inspection apparatus. In FIG. 4, a stage 101 has a liquid crystal substrate 100 supported thereon, and is the object to be inspected by the system. Substrate 100 is scanable in the Y axis direction. The beam emitted from a first light source 102 located directly above stage 101 travels through an illumination optical system 103, and then forms upon liquid crystal substrate 100 a band-shaped illumination region 104 having a shape that traverses liquid crystal substrate 100 in the X axis direction orthogonal to the scanning direction or Y axis direction.

The diffracted light from the pattern formed on the surface of liquid crystal substrate 100 in band-shaped illumination region 104 and the scattered light from defects or foreign matter adhering to the surface of liquid crystal substrate 100 are converged by a light receiving optical system 105. Light receiving optical system 105 has an optical axis 55 oriented in a direction that forms a predetermined angle with respect to the normal line of liquid crystal substrate 100, i.e. the Z axis. Optical axis 55 is located in a plane parallel to the scanning direction, i.e. the direction of the Y axis direction. An image from the scattered light from the irradiation region 104 is formed on a light receiving element 106, which can be a one-dimensional CCD. Light receiving element 106 is arranged so that the pixels (not shown), which are arranged longitudinally, are lined up in a direction substantially orthogonal to the scanning direction of the image of liquid crystal substrate 100, i.e. the direction of the X axis. The light intensity signal from light receiving element 106 is successively read and then stored in a memory apparatus 107 on the command of a signal of a control system 114 of stage 101 in electronic communication therewith.

In addition, a second light source 108 is arranged at a position offset from that of first light source 102 at a position above stage 101. The optical axis 54 of light source system 108 and illumination optical system 109 is in a plane that includes an optical axis 53 of illumination optical system 103 and optical axis 55 of light receiving optical system 105. The light generated by second light source 108 travels via second illumination optical system 109 and forms a second illumination region 110 on liquid crystal substrate 100 without overlapping first illumination region 104. The diffracted light in illumination band 110 from the pattern (not shown) formed on the surface of liquid crystal substrate 100 and the scattered light from defects and foreign matter adhering to the surface of liquid crystal substrate 100 are converged by a light receiving optical system 111. Light receiving optical system 111 has an optical axis 56 oriented in a direction that forms a predetermined angle with respect to the normal line of liquid crystal substrate 100, the Z axis, and is located in a plane that is parallel to the scanning direction of liquid crystal substrate 100, the Y Axis. The light converged by light receiving optical system 111 is then form into an image of the illumination region 110 on a light receiving element 112. Light receiving element 112 can be a one-dimensional CCD, similar to light receiving element 106. The light intensity signal is stored in a memory apparatus 113 on command of a signal from a control system 114 of stage 101 in electronic communication therewith, in the same manner as in first light receiving system 105.

Light generating systems 103 and 109 as well as light receiving systems 105 and 111 are positioned so that the region 104 on the surface of liquid crystal substrate 100 detected by first light receiving element 106 via first light receiving system 105 and the region 110 on the surface of liquid crystal substrate 100 detected by second light receiving element 112 via second light receiving system 111 do not overlap. Thus, in the example shown in FIG. 4, the two regions 104 and 101 are formed so that they are not offset in the X direction they do not overlap in the direction of the Y axis due to their offset position in the direction of the Y axis.

The wavelengths of light generated by first optical system 103 and second optical system 109, respectively, may be different and the system of the present invention will still work. System 103 and 109 may form different angles between their respective optical axes and the optical axes of their respective light receiving optical systems 105 and 111 and the normal line of liquid crystal substrate 100, and the system will still function properly. Also, both of the preceding conditions of different wavelengths and different angles formed by their respective optical axes and the system can be present and the method of the present invention will still function properly.

Given the irregularity of defects and foreign matter adhering to liquid crystal substrate 100, and the fact that they are not isometrically or uniformly shaped, they generally scatter light in a highly irregular pattern. Thus, an inspection apparatus positioned at a predetermined angle with the normal to the substrate 100 might not detect the presence of some of the defects and foreign matter adhering to liquid crystal substrate 100. To remedy this problem a plurality of light receiving systems can be employed with the optical axis of each set at a different angle to the normal line of the liquid crystal substrate, the Z axis, to detect the irregularly scattered light.

Situations may arise where no scattered light is detected from dust or foreign matter on the substrate. This condition can be caused by interference resulting from a thin film on the substrate such as the resist film formed on the substrate which may cancel certain wavelengths of light. Use of light of different wavelengths produced by different optical systems can remedy the problem.

Use of a plurality of detection optical systems with various illumination optical systems which create illumination regions which overlap lower the detection sensitivity of the over all system. To avoid this the preferred embodiment of the present invention calls for creation of detection regions which do not overlap to maintain the high detection sensitivity of the system.

Since the patterns on liquid crystal substrates have improved and become finer over the years, the conditions for inspection have changed, requiring more versatile inspection systems. Thus, the preferred embodiment of the present invention calls for inspection apparatus in which the the angle formed between the optical axis of the light receiving system and the normal line to the liquid crystal substrate can be variable. Additionally, the preferred embodiment calls for inspection systems that allow the free selection of different wavelengths of light to conduct the inspections.

The embodiments for carrying out the present invention described above, for ease of description, used examples that generally only had two irradiation optical systems and light receiving systems. However, three or more optical systems can significantly improve performance. Increasing the number of illumination and inspection optical systems allows for the inspection of a larger surface area and the performance of a greater variety of inspections. In addition, it is understood that the relationships between each of the irradiation regions 51A and 51B and each of the take-in regions 23A and 23B, shown in FIG. 5A to FIG. 5C, are not limited to the example shown in FIG. 1, but are also applicable to the examples shown in FIG. 3 and FIG. 4.

Figure 6:
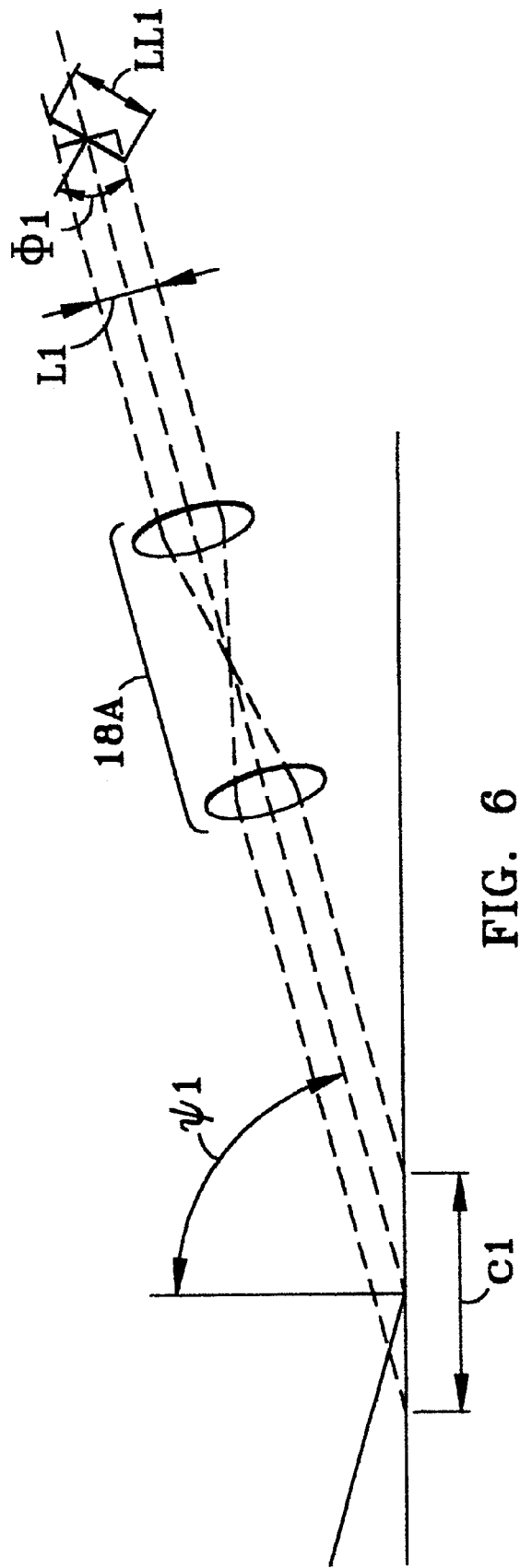
FIG. 6 is a view that illustrates the relationship between the light receiving surface and the band-shaped light take-in region.
Figure 7:
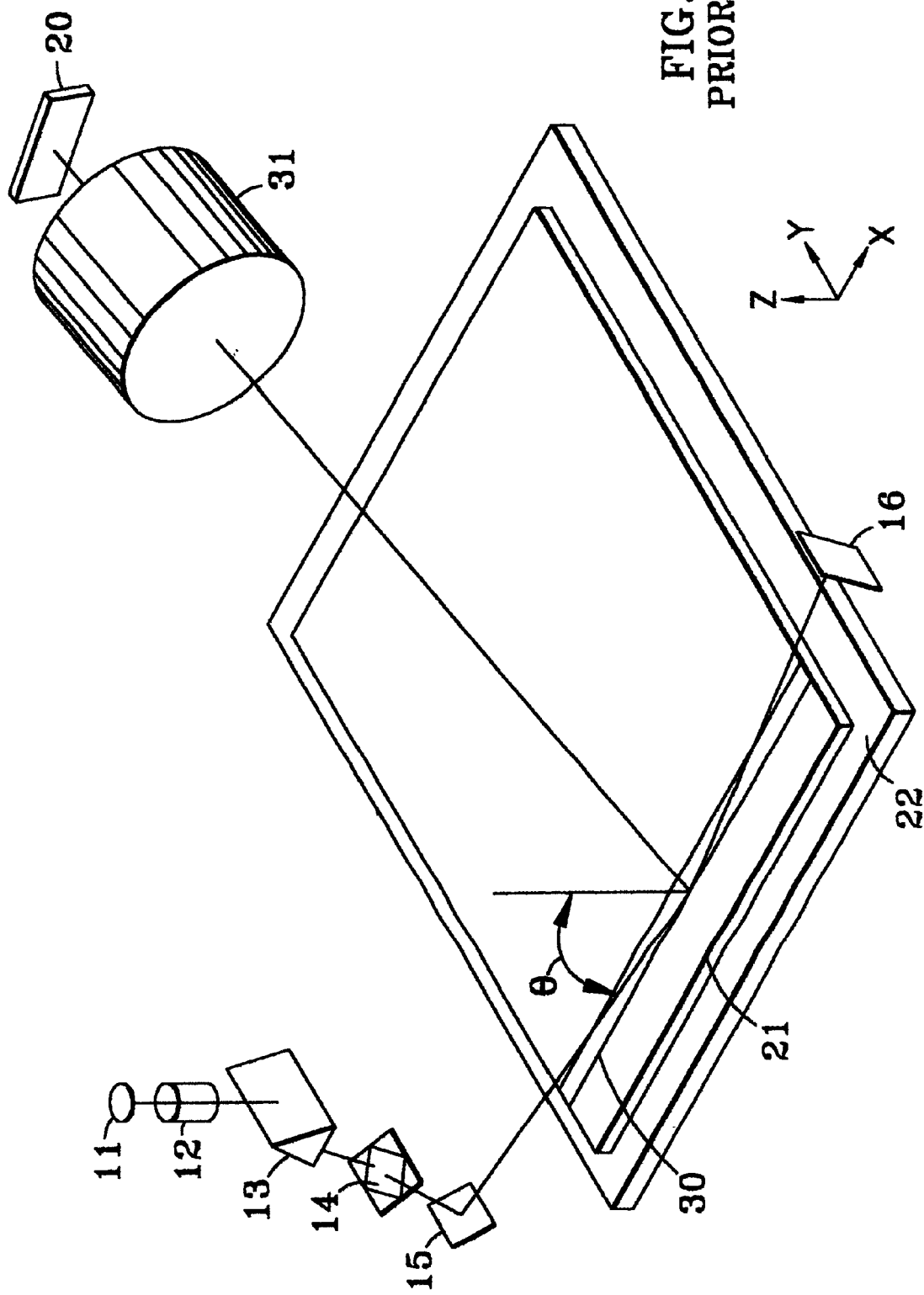
FIG. 7 is a schematic perspective view of a conventional prior art surface inspection apparatus.

The following explains the relationship between the light receiving surface and the band-shaped light receiving take-in region. Referring to FIG. 6, the condition $c1=L1/(\beta1 \cdot \cos \psi1)$ is satisfied, wherein L1 is the length in the direction perpendicular to the optical axis of the first light receiving surface in the scanning direction of the image on the first light receiving member of the surface to be inspected, $\beta1$ is the magnification of first light receiving optical system 18A, c1 is the width of the first band-shaped light receiving take-in region, and $\psi1$ is the angle between the normal line of the surface to be inspected in the first irradiation region and the optical axis of first light receiving optical system 18A. Likewise, the condition $c2=L2/(\beta2 \cdot \cos \psi2)$ is satisfied for the second light receiving member.

Accordingly, the condition which must be satisfied to assure that the first and second band-shaped light receiving take-in regions do not mutually overlap is $d>(L1/\beta1 \cdot \cos \psi1)+L2/(\beta2 \cdot \cos \psi2))/2$, wherein d is the distance between the centerlines of the first and second band-shaped light receiving take-in regions.

An example will help illustrate the significance of the preceding discussion, assume a centerline spacing d of the irradiation regions or the light receiving take-in regions 23 is 57.4 mm or greater so that the light receiving regions do not overlap based on the relationship in the condition mentioned above. Width b1 of the first band-shaped irradiation region and width b2 of the second band-shaped irradiation region are each 5 mm, length L1 of the first light receiving surface and length L2 of the second light receiving surface are each 0.5 mm, light receiving angle $\psi1$ of the first light receiving optical system (first detection optical system) and light receiving angle $\psi2$ of the second light receiving optical system (second detection optical system) are each 85°, and imaging magnification $\beta1$ of the first light receiving optical system (first detection optical system) and imaging magnification $\beta2$ of the second light receiving optical system are each 0.1×.

Additionally, when the light receiving surface of the first light receiving member is inclined by just angle $\phi1$ with respect to the optical axis of first light receiving system 18A (for example, when the light receiving surface is inclined so that the Scheimpflug condition is satisfied since the surface to be inspected is inclined with respect to the optical axis of the light receiving system), then the condition $L1=LL1 \cdot \cos \phi1$ is satisfied, wherein LL1 is the width of the light receiving surface. Accordingly, the following condition when the first and second band-shaped light receiving take-in regions do not mutually overlap is $d>(LL1 \cdot \cos \phi1/(\beta1 \cdot \cos \psi1)+LL2 \cdot \cos \psi2/(\beta2 \cdot \cos \psi2))/2$.

Additionally, the condition that the band-shaped irradiation region on one side and the band-shaped light receiving take-in region on the other side do not mutually overlap can be expressed by the same numerical expression. For example, the conditions $d1>(b1+c2)/2$ and $d2>(b2+c1)/2$ explained earlier can also be expressed as $d1>(b1+L2/(\beta2 \cdot \cos \psi2))/2$ and $d2>(b2+L1/(\beta1 \cdot \cos \psi1))/2$, as well as by $d1>(b1+LL2 \cdot \cos \phi2/(\beta2 \cdot \cos \psi2))/2$ and $d2>(b2+LL1 \cdot \cos \phi1/(\beta1 \cdot \cos \psi1))/2$.

In the embodiments of the present invention, a large inspection range is partitioned into a plurality of smaller inspection ranges, and the projecting of light onto and the receiving of light from each individual partitioned inspection ranges is accomplished with one set of optical systems for each. Thus, each individual irradiation system and light receiving system can be made extremely compact since the inspection range handled by one set of optical systems is reduced in size. However, by employing a plurality of optical systems, the number of parts increases. But, since each part is not significantly large and the parts are interchangeable among systems, yield in the fabrication process are improved and cost reduced. Also, since one set of irradiation systems corresponds to one set of light receiving systems, a reduction in the quantity of light that illuminates the object to be inspected can be avoided.

In the inspection apparatuses shown in FIG. 1 to FIG. 6, examples were explained wherein two sets of inspection optical systems are arranged so that each light receiving take-in region does not overlap the illumination region of the adjacent inspection optical system.

Figure 8A:
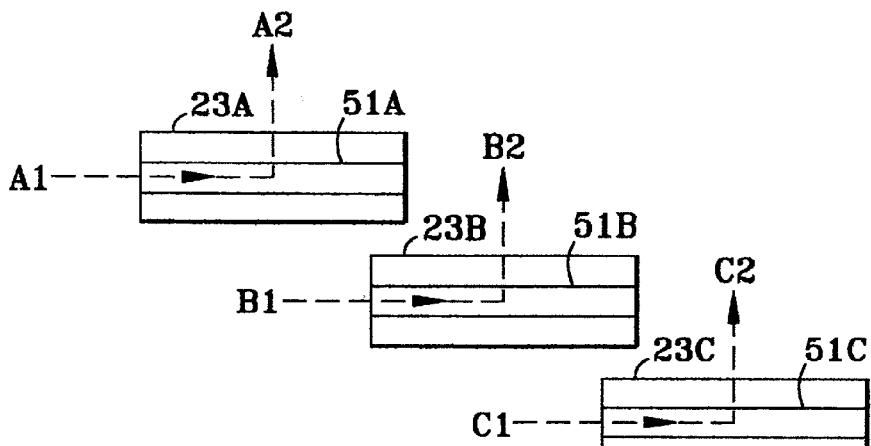
FIG. 8 (A) is a schematic plan view of an embodiment of the present invention which uses three sets of detection optical systems each of which is arranged so that light receiving take-in regions do not overlap adjacent irradiation regions on the surface to be inspected.
Figure 8B:
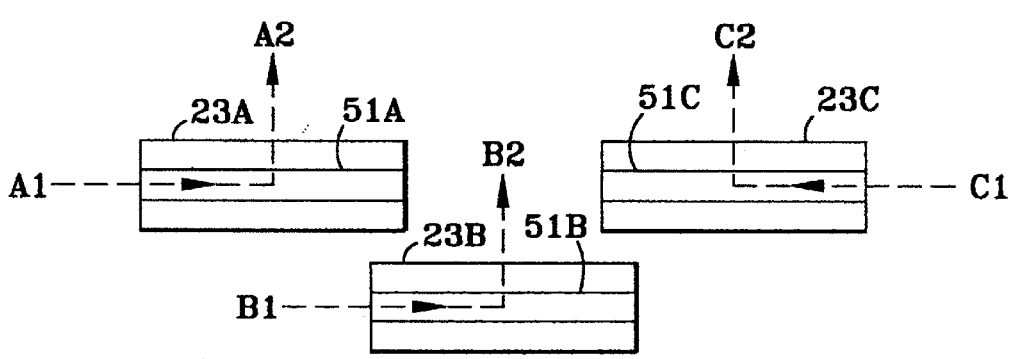

As previously noted, the present invention is not limited to the preceding examples which for the most part describe the present invention using just two pairs of inspection optical systems. Practice of the present invention allows and even encourages employment of three sets, four sets and even more sets of inspection optical systems. However, to assure the proper functioning of the system of the present invention, the preferred embodiment requires arrangement of the plurality of inspection optical systems so that adjacent light receiving take-in regions do not overlap adjacent illumination regions on the surface to be inspected. For example, FIG. 8A and FIG. 8B depict the situation where three sets of inspection optical systems are arranged so that take in or light receiving regions 23A, 23B and 23C and illumination regions 51A, 51B and 51C do not mutually overlap on the surface to be inspected. Thus, FIG. 8A and FIG. 8B show an aspect wherein three sets of inspection optical systems are arranged so that other illumination regions do not overlap neighboring light receiving take-in regions on the surface to be inspected.

Accordingly, first illumination region 23A is formed on the surface to be inspected by first irradiation system A1, and first illumination region 51A exists in first light receiving take-in region 23A of first light receiving system A2 on the surface to be inspected. In other words, first light receiving take-in region 23A is larger than first illumination region 51A. Second illumination region 23B is formed on the surface to be inspected by second irradiation system B1, and second illumination region 51B exists in second light receiving take-in region 23B of second light receiving system B2 on the surface to be inspected. In other words, second light receiving take-in region 23B is larger than second illumination region 51B. Third illumination region 23C is formed on the surface to be inspected by a third irradiation system C1 not shown, and third illumination region 51C exists in third light receiving take-in region 23B of third light receiving system C2 on the surface to be inspected. In other words, third light receiving take-in region 23C is larger than third illumination region 51C.

Referring to FIG. 5A, if the system is configured such that a specific irradiation region and the inspection region viewed by one set of optical systems is made to overlap with respect to the surface to be inspected by a set amount a so as to prevent omissions in the detection of foreign matter, then the overlap portion a is strongly irradiated by the light beams and the detected scattered light intensity unfortunately varies dependent on changes in the irradiation intensity (namely, dependent on the position at which foreign matter adheres). In such a case, the detection sensitivity of foreign matter is not uniform, which results in the loss of reproducibility and reliability of foreign matter inspection. To avoid this problem, each photoelectric detection system is installed to function separately in the scanning direction according to the mode for carrying out the present invention.

The apparatus of the modes for carrying out the present invention described above are ideally suited as foreign matter inspection apparatuses for automatically inspecting foreign matter adhering to the surface of a foreign matter adhesion prevention thin film (pellicle) stretched across in parallel to a photomask or reticle and the like, particularly those used in the fabrication process of integrated circuits. Using the inspection apparatuses shown in FIG. 1 to FIG. 6 and in FIG. 8 and inspecting with high precision the surface of a reticle (or mask) whereon a predetermined pattern (circuit pattern and the like) is formed ultimately enables the manufacture of satisfactory liquid crystal display apparatuses, semiconductor devices, thin film magnetic heads and the like, while improving yield.

Figure 9:
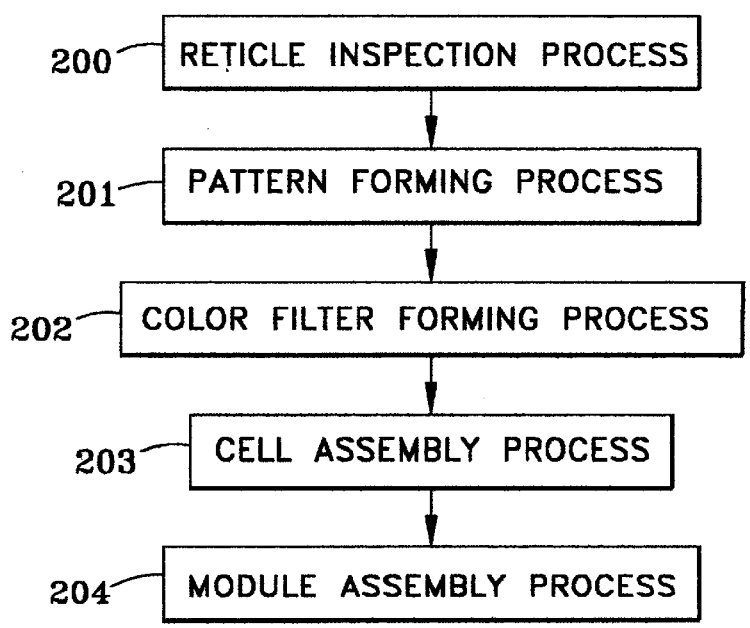
FIG. 9 is block diagram which depicts the steps for manufacture of a liquid crystal display manufacturing method which uses the inspection apparatus according to the present invention.

The following explains a liquid crystal display apparatus manufacturing method that uses the inspection apparatus according to the present invention, referencing FIG. 9. Reticle inspection process 200 uses the inspection apparatuses shown in FIG. 1 to FIG. 6 and in FIG. 8 to inspect a reticle whereon a predetermined pattern (circuit pattern and the like) is formed. In process 200, the system of the present invention checks for the presence of foreign matter adhering to the reticle surface. Based this inspection, the system determines if the surface is free of dust and other foreign matter and the next step in the photolithography process the pattern forming process 201 can be conducted. If after inspection it determines the reticle has dust or other foreign matter on it, the system conducts a foreign matter removal process. After the foreign matter adhering to the reticle is removed by the foreign matter removal apparatus in the foreign matter removal process the reticle is again inspected in reticle inspection process 200. Once the inspection process verifies the surface is clear of any dust or foreign matter in inspection process 200, the system then moves onto pattern forming process 201.

In pattern forming process 201, the so-called photolithography process is executed wherein, principally, the pattern on a reticle is transferred and exposed onto a photosensitive substrate (glass substrate and the like whereon a resist is coated) using an exposure apparatus. By this photolithography process, a predetermined pattern that includes numerous electronic devices and the like are formed on the photosensitive substrate. Subsequently, the exposed substrate passes through the various semiconductor manufacturing processes including the etching process and reticle stripping process whereby a predetermined pattern is formed on the substrate. Once these are completed, the system commences a color filter forming process 202.

The photolithography process can use a proximity-type exposure apparatus that brings a reticle and photosensitive substrate into close contact and exposes them, or a projection exposure type exposure apparatus that uses a projection optical system to project the pattern image of a reticle onto a photosensitive substrate. Furthermore, a projection exposure type exposure apparatus can employ a step-and-repeat system, a scanning exposure system that performs exposure while moving the reticle and photosensitive substrate with respect to the projection optical system, and the like. Color filter forming process 202 forms color filters wherein numerous sets of three dots, corresponding to R (Red), G (Green) and B (Blue), are arrayed in a matrix. In addition, a cell assembly process 203 is executed after color filter forming process 202. In cell assembly process 203, a liquid crystal panel (liquid crystal cell) is assembled using a substrate having a predetermined pattern obtained in pattern forming process 201, color filters obtained in color filter forming process 202, and the like. In cell assembly process 203, a liquid crystal panel (liquid crystal cell) is manufactured by, for example, injecting liquid crystal between the substrate having a predetermined pattern obtained in pattern forming process 201 and the color filters obtained in color filter forming process 202. Subsequently, in a module assembly process 204, the liquid crystal display device is completed by attaching each of the parts like the electric circuit that performs the display operation of the assembled liquid crystal panel (liquid crystal cell), and the backlight. By passing through each of the processes shown in FIG. 9, satisfactory liquid crystal display elements and the like can be manufactured while improving yield.

According to the present invention as described above, since the first band-shaped irradiation region and the second band-shaped irradiation region are formed on the surface to be inspected deviated by just a predetermined distance along a predetermined direction (second direction, Y), it is possible to assure that light from the first irradiation regions is not taken into the second light receiving system and light from the second irradiation system is not taken in by the first light receiving system, and the surface to be inspected can be inspected with a high degree of accuracy.

In addition, by adopting a configuration in which the first and second band-shaped irradiation regions are formed deviated along a direction (first direction, X) that intersects a predetermined direction, it is possible to cover and inspect a large surface to be inspected.

While the present invention has been described in connection with a preferred embodiment, it will be understood that it is not so limited. On the contrary, it is intended to cover all alternatives, modifications and equivalents as may be included within the spirit and scope of the invention as defined in the appended claims.

What is claimed is:

1. A liquid crystal display manufacturing method comprising:
   inspecting a reticle having a pattern thereon for defects and foreign matter adhering to the reticle; and
   exposing a pattern of the reticle onto a photosensitive substrate;
   wherein said step of inspecting the reticle comprises:
   a. irradiating the reticle with a first light beam from a first light irradiation system to form a first band-shaped irradiation region along a predetermined first direction on the reticle;
   b. receiving scattered light from said first band-shaped irradiation region with a first light receiving system;
   c. irradiating the reticle with a second light beam from a second light irradiation system to form a second band-shaped irradiation region along said first direction on the reticle;
   d. receiving scattered light from said second band-shaped irradiation region with a second light receiving system; and
   e. moving the reticle relative to said first and second light irradiation systems along a second direction substantially orthogonal to said first direction;
   f. wherein said first band-shaped irradiation region and said second band-shaped irradiation region are separated by a predetermined distance along said second direction so as to prevent said first light irradiation system from receiving scattered light from said second band-shaped irradiation region and prevent said second light irradiation system from receiving scattered light from said first band-shaped irradiation region.

2. A method according to claim 1, wherein the first band-shaped irradiation region and the second band-shaped irradiation region jointly scan the reticle without any gaps.

3. A method according to claim 1, wherein:
   a. said first light receiving system has a first optical system that forms an image of said first band-shaped irradiation region in a first imaging plane, and has a first light receiving member having a first light receiving surface at or near said first imaging plane;
   b. said second light receiving system has a second optical system that forms an image of said second band-shaped irradiation region in a second imaging plane, and has a second light receiving member having a second light receiving surface at or near said second imaging plane;
   c. said predetermined distance is set so that a first band-shaped light receiving take-in region on the reticle corresponding to said first light receiving surface with respect to said first light receiving system does not overlap said second irradiation region, and so that a second band-shaped light receiving take-in region on the reticle corresponding to said second light receiving surface with respect to said second light receiving system does not overlap said first irradiation region; and
   d. b1 is the width of said first band-shaped irradiation region, c1 is the width of said first band-shaped light receiving take-in region, b2 is the width of said second band-shaped irradiation region and c2 is the width of said second band-shaped light receiving take-in region, a distance between a center of said first-band-shaped irradiation region and a center of said second band-shaped light receiving take-in region is greater then the value of half of (b1+c2), and a distance between the center of said second band-shaped irradiation region and the center of said first band-shaped light receiving take-in region is greater than the value of half of (b2+c1).

4. A method according to claim 1, wherein:
   a. said first light receiving system has a first optical system that forms an image of said band-shaped irradiation region in a first imaging plane, and has a first light receiving member having a first light receiving surface at or near said first imaging plane;
   b. said second light receiving system has a second optical system that forms an image of said second band-shaped irradiation region in a second imaging plane, and has a second light receiving member having a second light receiving surface at or near said second imaging plane;
   c. a width of said first band-shaped irradiation region is narrower than a width of a first band-shaped light receiving take-in region on said reticle corresponding to said first light receiving surface with respect to said first light receiving system, and a width of said second band-shaped irradiation region is narrower than a width of a second band-shaped light receiving take-in region on the reticle corresponding to said second light receiving surface with respect to said second light receiving system; and
   d. said first band-shaped light receiving take-in region and said second band-shaped light receiving take-in region on said reticle do not overlap.

5. A method according to claim 1, wherein said first light irradiation system projects said first light beam toward the reticle at an angle of incidence in the range of between 80° to 90°, and said second light irradiation system projects said second light beam toward the reticle at an angle of incidence of between 80° to 90°, and wherein the angle of incidence is the angle formed between the normal to the reticle and the axis of illumination of the first and second light irradiation systems, respectively.

6. A liquid crystal display manufacturing method comprising:
   inspecting a reticle having a pattern thereon for defects and foreign matter adhering to the reticle; and
   exposing a pattern of the reticle onto a photosensitive substrate;
   wherein said step of inspecting the reticle comprises:
   a. forming a first illumination region on the reticle;
   b. detecting light from said first illumination region with a first detection region; said first detection region having a predetermined size on the reticle that is different from a size of said first illumination region on the reticle;
   c. forming a second illumination region on the reticle; and
   d. detecting light from said second illumination region with a second detection region, said second detection region having a predetermined size that is different from a size of said second illumination region.

7. A method according to claim 6, wherein:
   said step of detecting scattered light from the first illumination region includes detecting scattered light from a first detection region which includes said first illumination region and wherein said first detection region is larger than said first illumination region; and said step of detecting scattered light from the second illumination region includes detecting scattered light from a second detection region which includes said second illumination region and wherein said second detection region is larger than said second illumination region.

8. A method according to claim 7, wherein said step of forming said first and second illumination regions involves illuminating said first and second illumination regions so that the first and second illumination regions do not overlap on the reticle.

9. A method according to claim 6, wherein said step of forming said first and second illumination regions involves illuminating said first and second illumination regions so that the first and second illumination regions do not overlap on the reticle.

10. A liquid crystal display manufacturing method comprising:

inspecting a reticle having a pattern thereon for defects and foreign matter adhering to the reticle; and exposing a pattern of the reticle onto a photosensitive substrate;

wherein said step of inspecting the reticle comprises:

forming a first illumination region on the reticle;

forming a second illumination region on the reticle without overlapping said first illumination region;

detecting scattered light from said first illumination region without receiving scattered light from said second illumination region; and detecting scattered light from said second illumination region without receiving scattered light from said first illumination region.

11. A method according to claim 10, wherein said step of detecting scattered light from said first illumination region comprises the step of using a first detection region having a size on the reticle that is different from a size of said first illumination region; and wherein said step of detecting scattered light from said second illumination region comprises the step of using a detection region having a size on the reticle that is different from a size of said second illumination region.

* * * * *